(12) United States Patent
Zhang et al.

(10) Patent No.: US 7,018,559 B2
(45) Date of Patent: Mar. 28, 2006

(54) FUNCTIONAL FLUID COMPOSITIONS CONTAINING EPOXIDE ACID SCAVENGERS

(75) Inventors: Jingen Zhang, Collegeville, PA (US); Mark E. Jason, Longmeadow, MA (US); Terry C. Wolfe, Olivette, MO (US)

(73) Assignee: Solutia Inc., St. Louis, MO (US)

( * ) Notice: Subject to any disclaimer, the term of this patent is extended or adjusted under 35 U.S.C. 154(b) by 550 days.

(21) Appl. No.: 09/851,072

(22) Filed: May 8, 2001

(65) Prior Publication Data

US 2002/0033478 A1    Mar. 21, 2002

Related U.S. Application Data

(60) Provisional application No. 60/202,954, filed on May 9, 2000.

(51) Int. Cl.
*C09K 5/10* (2006.01)
*C09K 5/20* (2006.01)

(52) U.S. Cl. .......................... 252/73; 252/77; 252/78.1; 252/78.5; 252/79

(58) Field of Classification Search ................. 252/72, 252/73, 74, 75, 76, 77, 78.1, 78.3, 78.5, 79

See application file for complete search history.

(56) References Cited

U.S. PATENT DOCUMENTS

| | | |
|---|---|---|
| 3,487,020 A | 12/1969 | Peeler et al. |
| 3,723,320 A | 3/1973 | Herber et al. |
| 3,941,708 A | 3/1976 | Gentit et al. |
| 3,941,709 A | 3/1976 | Herber et al. |
| 3,976,585 A | 8/1976 | Herber et al. |
| 4,076,642 A | 2/1978 | Herber et al. |
| 5,464,551 A | 11/1995 | Deetman |

FOREIGN PATENT DOCUMENTS

| | | |
|---|---|---|
| EP | 0717098 A2 | 6/1996 |
| WO | WO 0022071 A1 | 4/2000 |

OTHER PUBLICATIONS

Johnson, Carl R. and Dutra, Gerard A.: "Reactions of Lithium Diorganocuprates (1) with Tosylates. 1. Synthetic Apsects" Journal of the American Chemical Society, vol. 95, No. 23, 1973, pp. 7777-7782, XP002182749, Nov. 14, 1973.

Chini, Marco, et al.: "Regiochemical Control of the Ring-Opening of 1, 2-Epoxides by Means of Chelating Process. 2. 'Synthesis and Reactions of the cis— and trans Oxides of 4-[ (Benzyloxy) methyl ] cyclohexene, 3-Cyclohexenemethanol, and Methyl 3-cyclohexenecarboxylate" Journal of Organic Chemistry, vol. 57, No. 5, 1992, pp. 1405-1412, XP002182750.

*Primary Examiner*—Gregory R. Del Cotto
(74) *Attorney, Agent, or Firm*—Blackwell Sanders Peper Martin LLP

(57) ABSTRACT

A phosphate ester-based functional fluid composition that generates reduced levels of carboxylic acid during use by incorporating at least one acid scavenger selected from the epoxides of the invention. The phosphate ester-based functional fluids are particularly useful as hydraulic fluids.

9 Claims, 7 Drawing Sheets

FUNCTIONAL FLUID COMPOSITIONS CONTAINING EPOXIDE ACID SCAVENGERS

RELATED APPLICATION

This application is a nonprovisional application which claims the priority under 35 USC 119(e) of prior provisional application Ser. No. 60/202,954, entitled "Functional Fluid Compositions Containing Epoxide Stabilizers", filed May 9, 2000, which is hereby incorporated by reference into this application.

BACKGROUND OF THE INVENTION

This invention relates to improved functional fluid compositions containing epoxides useful as acid scavengers. This invention further relates to phosphate ester-based functional fluids, particularly phosphate ester-based hydraulic fluids, containing the epoxide acid scavengers of this invention.

In the past, functional fluids have been utilized as electronic coolants, diffusion pump fluids, lubricants, damping fluids, bases for greases, power transmission and hydraulic fluids, heat transfer fluids, heat pump fluids, refrigeration equipment fluids, and as a filter medium for air-conditioning systems. Hydraulic fluids intended for use in the hydraulic system of aircraft for operating various mechanisms and aircraft control systems must meet stringent functional and use requirements. Among the most important requirements of an aircraft hydraulic fluid is that it be stable against oxidative and hydrolytic degradation at elevated temperatures.

U.S. Pat. Nos. 3,723,320, 3,941,708, and 5,464,551 disclose epoxide acid scavengers for use in phosphate ester-based functional fluids and teach that the preferred epoxides are 3,4-epoxycycloalkyl carboxylates. These 3,4-epoxycycloalkyl carboxylates are typically used in current commercial phosphate ester-based functional fluid compositions and these fluids are susceptible to formation of carboxylic acids during use. During use of phosphate ester-based functional fluids, carboxylic acid levels increase and cause the useful life of the fluid to be reduced. While the '320 patent discloses —CH2OR and —C(O)R substituted epoxycyclohexyl compounds as one of numerous epoxycyclohexyl compounds in its generic epoxide formula, and the '708 patent discloses —CH2OR substituted epoxycycloalkyl compounds as one of numerous epoxycycloalkyl compounds in its generic epoxide formula, neither patent discloses or suggests either the problem of carboxylic acid formation nor a solution for this problem.

There exists a need for improved epoxide acid scavengers and for improved phosphate ester-based functional fluids containing such epoxide acid scavengers that generate less carboxylic acid during use of the functional fluids. There also exists a need for such improved epoxide acid scavengers to have an acceptable rate of depletion when compared to the currently used 3,4-epoxycycloalkyl carboxylates. It has now been discovered that the phosphate ester-based functional fluid compositions of the invention containing the epoxides of the invention generate less carboxylic acids during use of the functional fluids while having an acceptable depletion rate during use.

SUMMARY OF THE INVENTION

It is an object of this invention to provide novel epoxide compounds useful as acid scavengers, more particularly useful in phosphate ester-based functional fluids. It is another object of the invention to provide improved fluid life functional fluids that generate less carboxylic acid when the functional fluid is used in a use environment. It is a further object of the invention to provide a method for increasing the fluid life of phosphate ester-based functional fluids by incorporating the acid scavengers of the invention into the functional fluid composition. The above and other objects are met in this invention, described in more non-limiting detail hereinafter.

According to the invention, functional fluid composition that generates reduced levels of carboxylic acid during use is provided comprising a basestock comprising a phosphate ester, and at least one acid scavenger selected from epoxides of formula (I) (as described herein), epoxides of formula (II) (as described herein), or mixtures thereof; wherein $R^1$, $R^2$ and $R^3$ are independently selected from H, $—(CH_2)_n—R$ and $—C(O)—R^{12}$, and wherein one or two of $R^1$, $R^2$ and $R^3$ are $—C(O)—R^{12}$ or $—(CH_2)_n—R$; $R^4$ is selected from H or $—CH_3$; and $R^5$, $R^6$, $R^7$ and $R^8$ are independently selected from H, $—(CH_2)_n—R$ and $—C(O)—R^{12}$, and wherein up to two of $R^5$, $R^6$, $R^7$ and $R^8$ are $—C(O)—R^{12}$ or $—(CH_2)_n—R$; wherein R is selected from H, a linear or branched alkyl group having 1 to 12 carbon atoms, an arylalkyl group having 7 to 12 carbon atoms, $—O—R^{10}$, $—O—R^9—O—R^{10}$,

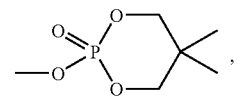

or $—Si—(OR^{11})_3$; $R^{12}$ is selected from a linear or branched alkyl group having 1 to 12 carbon atoms, or an arylalkyl group having 7 to 12 carbon atoms, n is an integer from 1 to 4, $R^9$ is an alkylene group having 2 to 6 carbon atoms, $R^{10}$ is an alkyl group having 1 to 12 carbon atoms, $R^{11}$ is an alkyl group having 1 to 8 carbon atoms, and $R^{12}$ is an alkyl group having 1 to 12 carbon atoms.

Further according to the invention, a method for reducing the production of carboxylic acid during use of a functional fluid is provided, the functional fluid comprising a basestock comprising a phosphate ester, and at least one acid scavenger, the method comprising admixing at least one acid scavenger selected from epoxides of the invention in the phosphate ester-based functional fluid.

BRIEF DESCRIPTION OF THE DRAWINGS

FIG. 1 is a plot of epoxide depletion for MCS 1562 and EOH in accordance with the Kinetic Study Procedure.

FIG. 2 is a plot of epoxide depletion for MCS 1562, ENB and TMOE in accordance with the Kinetic Study Procedure.

FIG. 3 is a plot of epoxide depletion for MCS 1562, BOCH, DOCH, BEOCH in accordance with the Kinetic Study Procedure.

FIG. 4 is a plot of epoxide depletion for MCS 1562 and DODOH in accordance with the Kinetic Study Procedure.

FIG. 5 is a plot of epoxide depletion for MCS 1562, KHOH, KPOH, and MHOCH in accordance with the Kinetic Study Procedure.

FIG. 6 is a plot of epoxide depletion for MCS 1562 and BOBH in accordance with the Kinetic Study Procedure.

FIG. 7 is a plot of epoxide depletion for MCS 1562 and OMOO in accordance with the Kinetic Study Procedure.

DETAILED DESCRIPTION OF THE INVENTION

Figure 1:
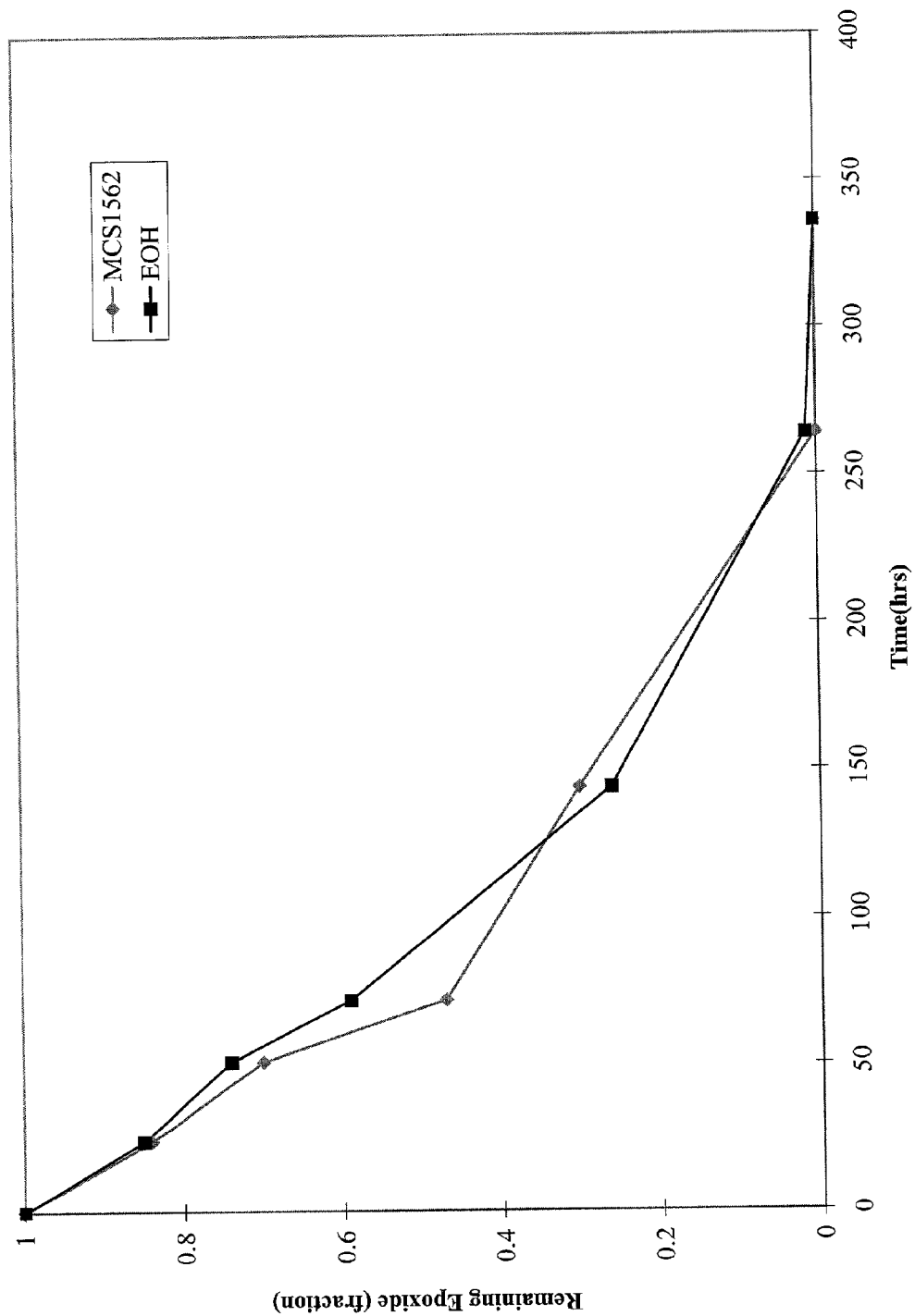
FIGS. 1 to 7 are plots of epoxide depletion data as a function of elapsed time for formulations illustrative of this invention compared to control epoxide MCS 1562 that were tested under conditions in accordance with Kinetic Study Procedure described hereinafter.
Figure 2:
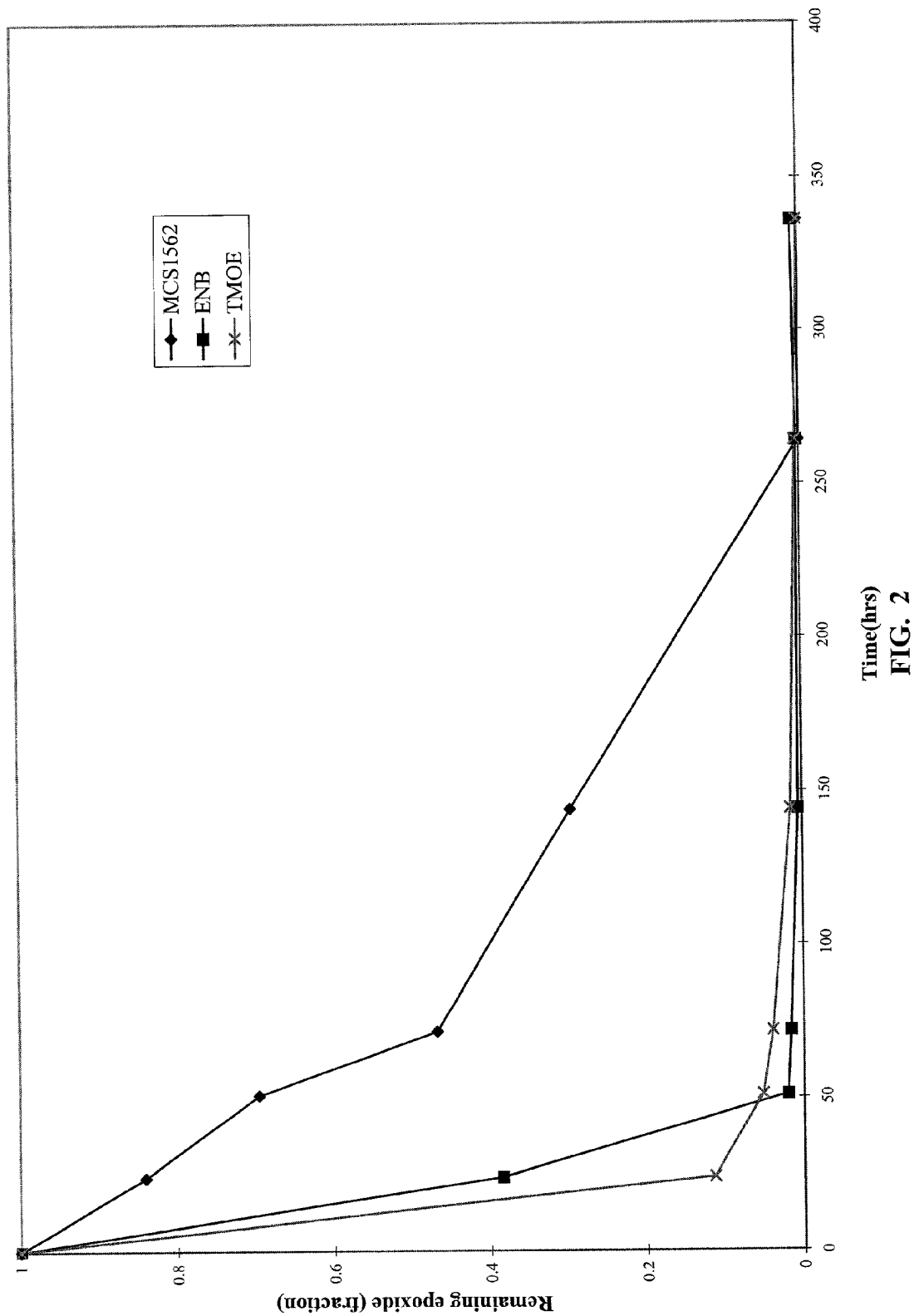
Figure 3:
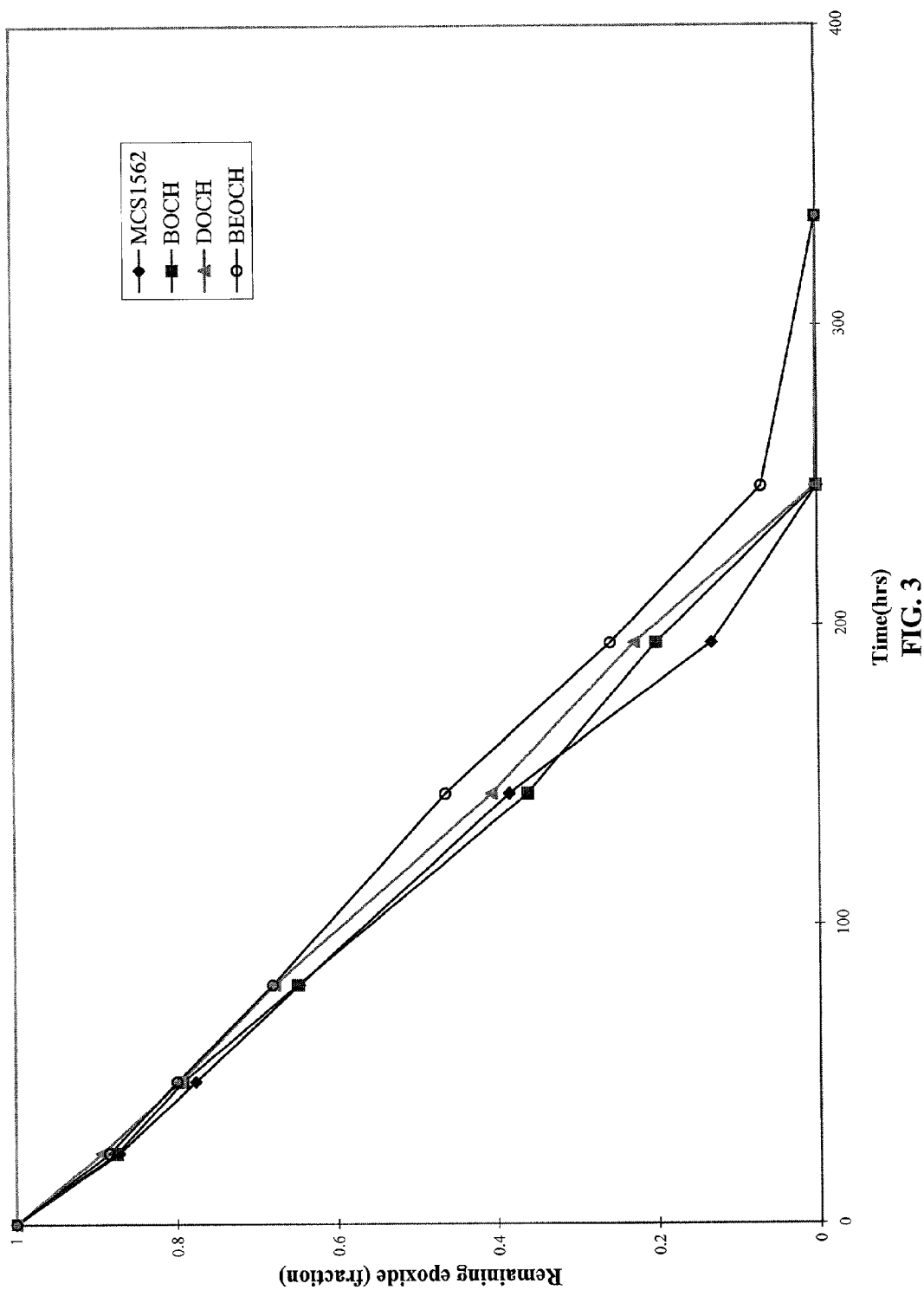
Figure 4:
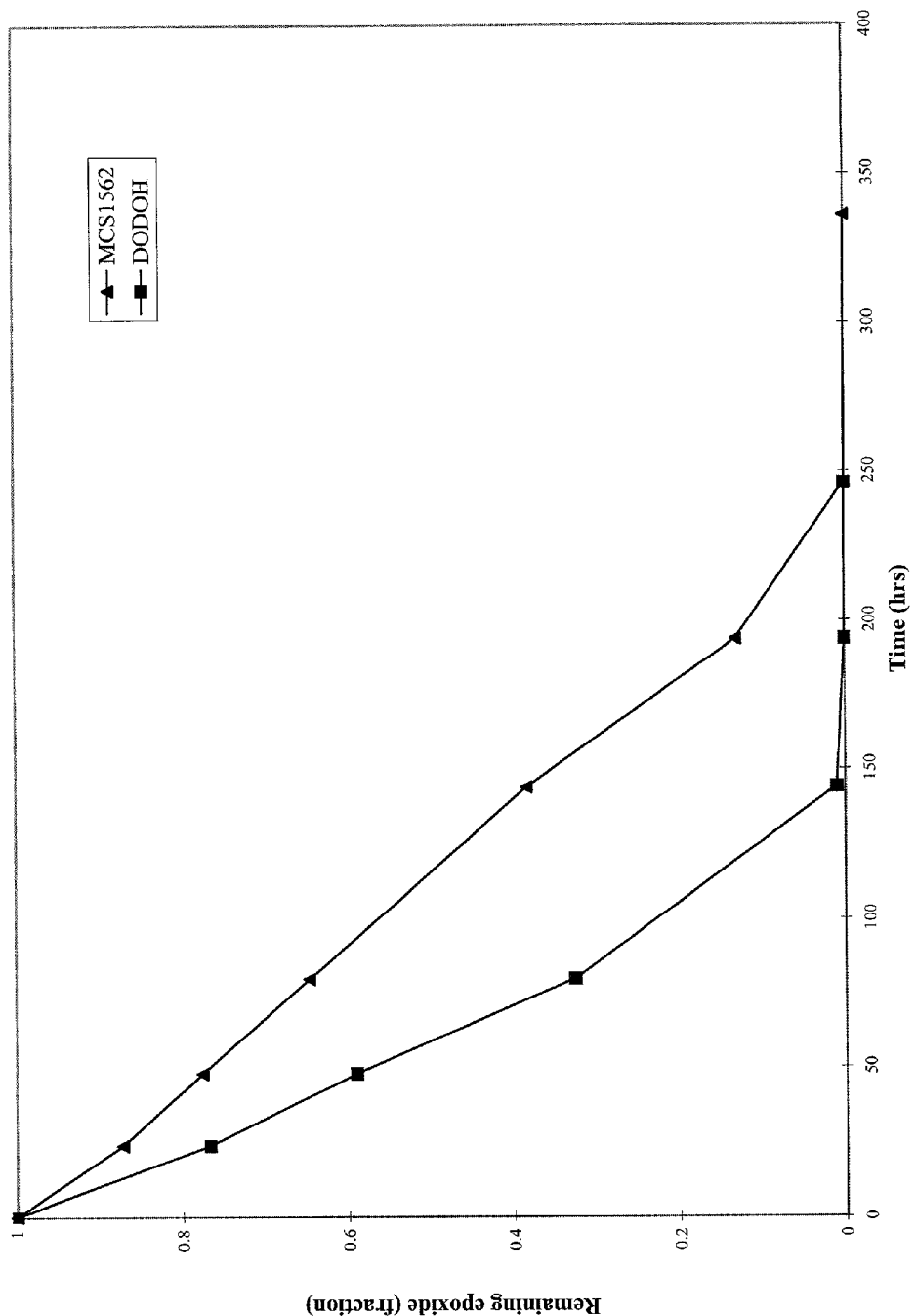
Figure 5:
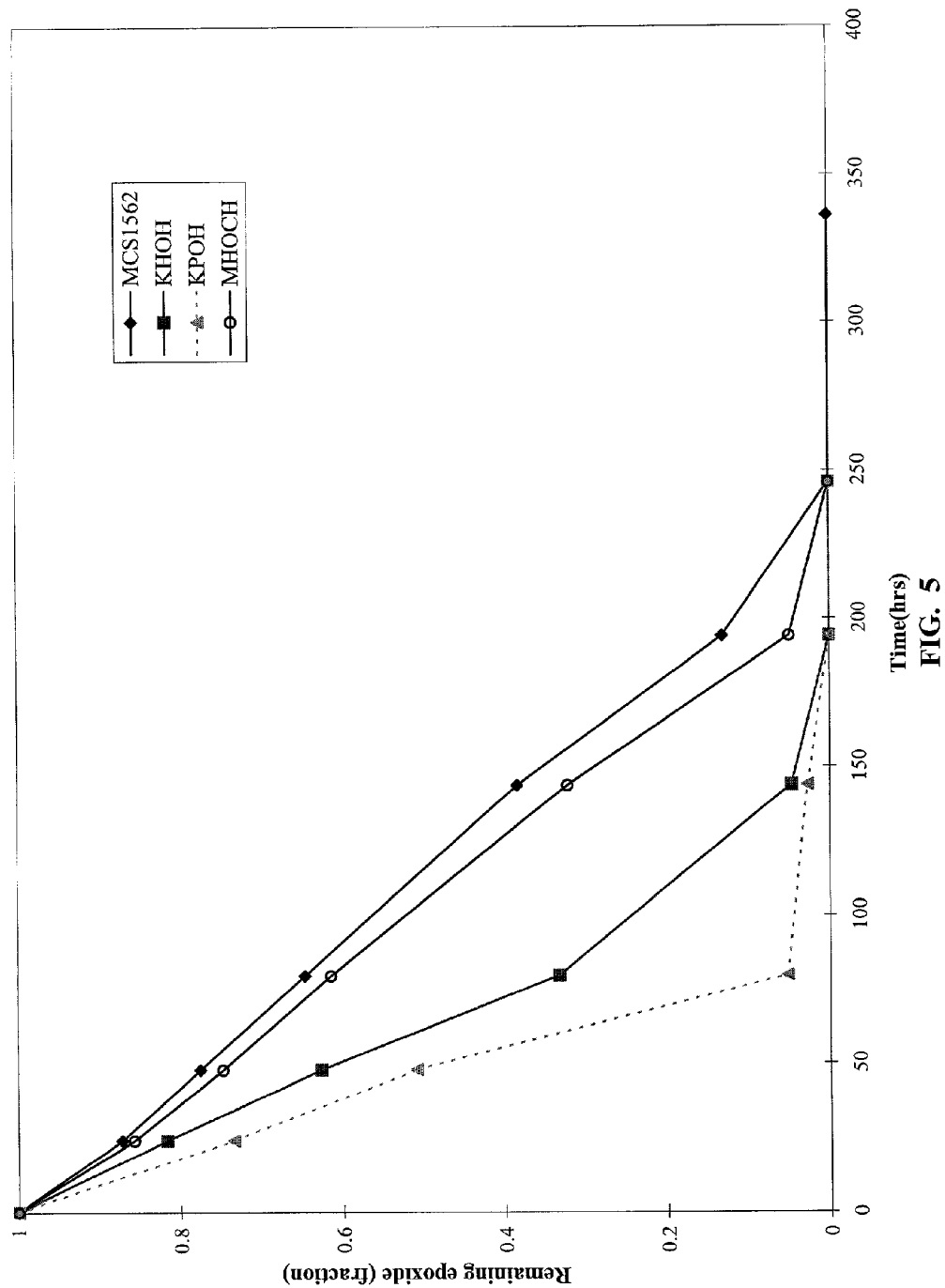
Figure 6:
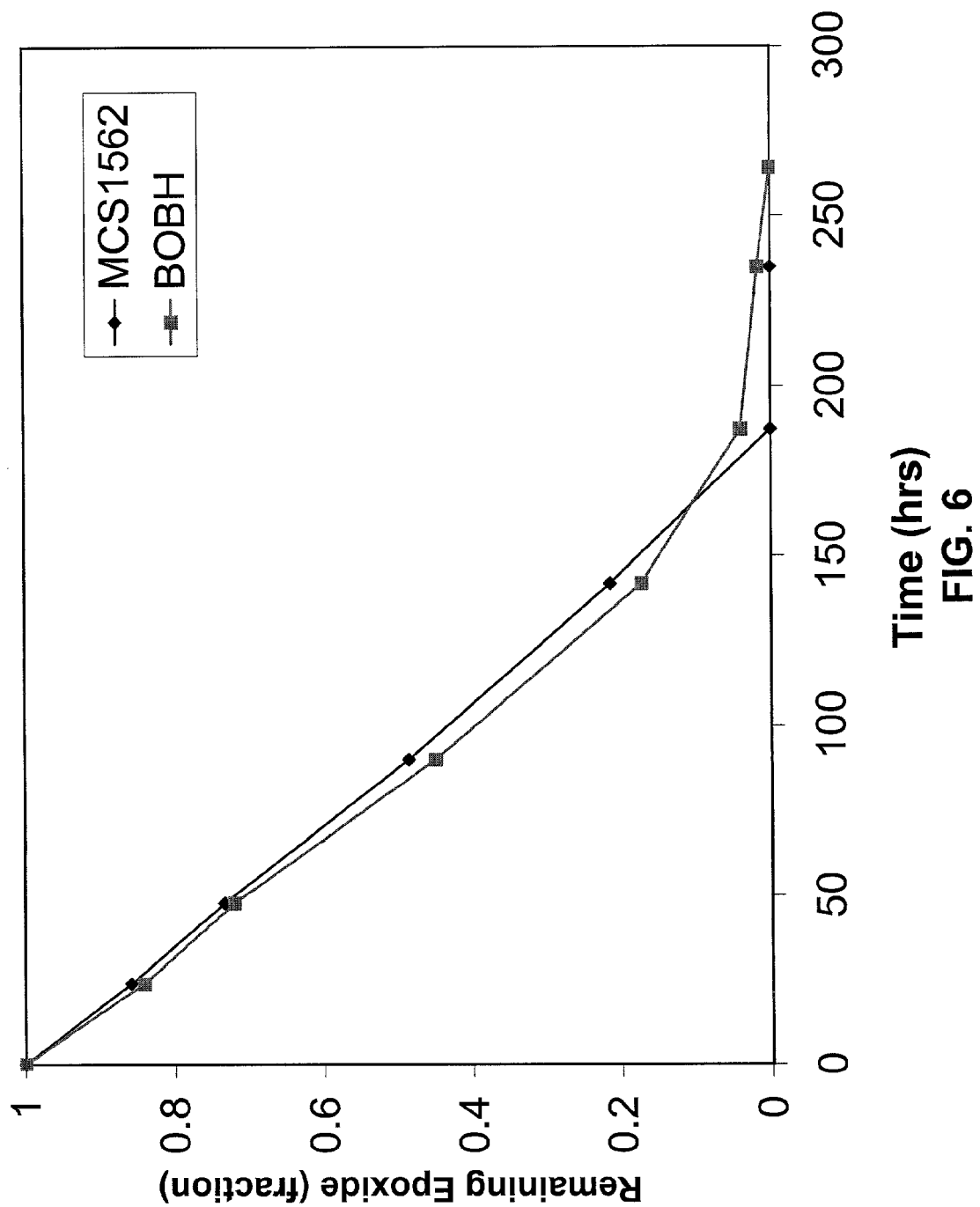
Figure 7:
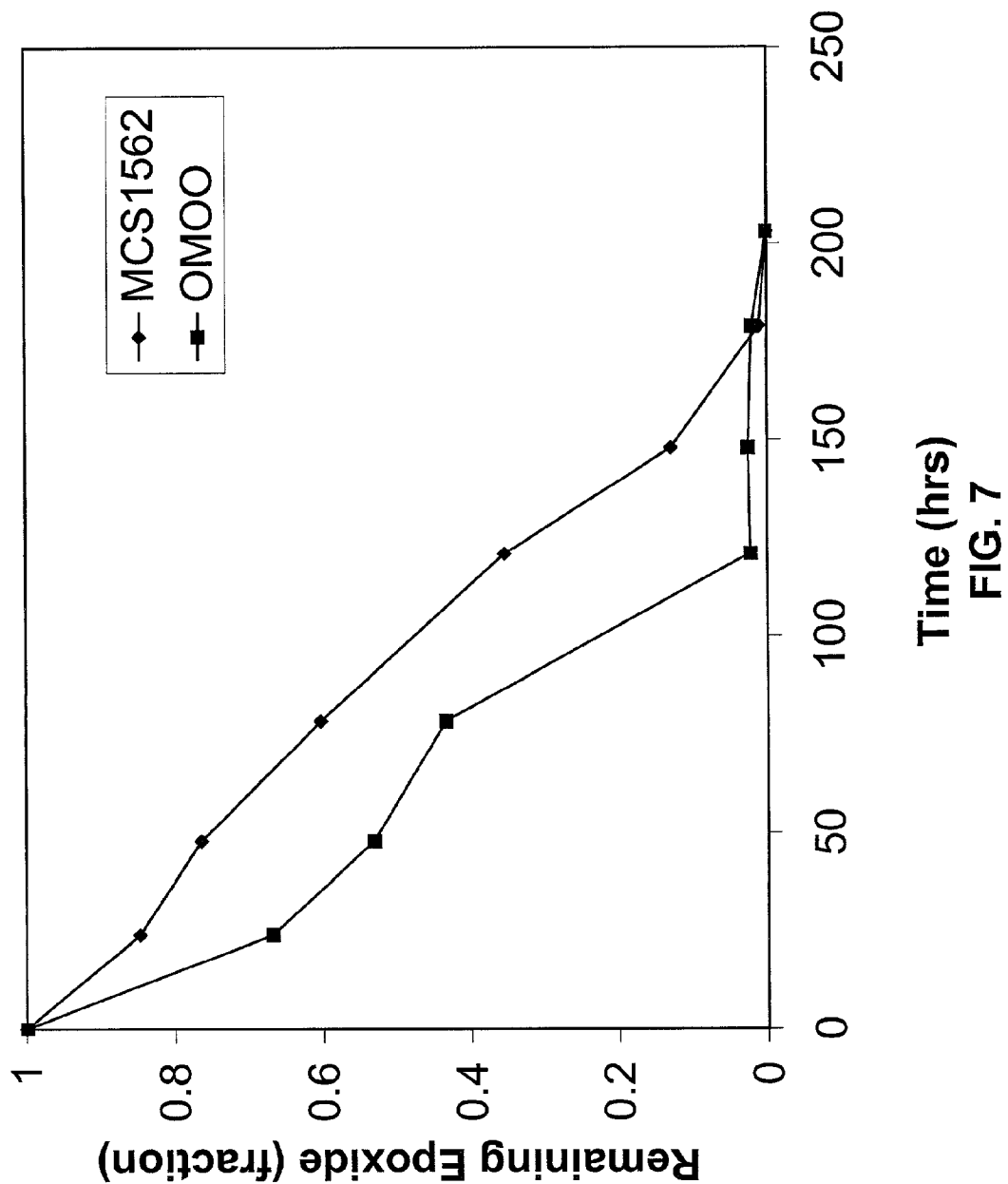

A first embodiment of the invention relates to a functional fluid composition that generates reduced levels of carboxylic acid during use comprising: (a) a basestock comprising a phosphate ester, and (b) at least one acid scavenger selected from (i) epoxides of the formula

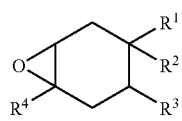

(I)

(ii) epoxides of the formula

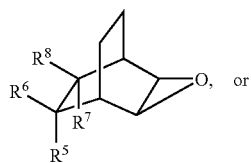

(II)

(iii) mixtures thereof.

$R^1$, $R^2$ and $R^3$ are independently selected from H, —$(CH_2)_n$—R and —C(O)—$R^{12}$, and one or two of $R^1$, $R^2$ and $R^3$ are —C(O)—$R^{12}$ or —$(CH_2)_n$—R, preferably —$(CH_2)_n$—R. In one embodiment $R^1$ and $R^2$ are —C(O)—$R^{12}$ or —$(CH_2)_n$—R, preferably —$(CH_2)_n$—R. In another embodiment $R^1$ and $R^3$ are —C(O)—$R^{12}$ or —$(CH_2)_n$—R, preferably —$(CH_2)_n$—R. In a preferred embodiment, one of $R^1$, $R^2$ and $R^3$ is —C(O)—$R^{12}$ or —$(CH_2)_n$—R. $R^4$ is selected from H or —$CH_3$, preferably H. $R^5$, $R^6$, $R^7$ and $R^8$ are independently selected from H, —$(CH_2)_n$—R and —C(O)—$R^{12}$, and up to two of $R^5$, $R^6$, $R^7$ and $R^8$ are —C(O)—$R^{12}$ or —$(CH_2)_n$—R. In a preferred embodiment, one of $R^5$, $R^6$, $R^7$ and $R^8$ is —C(O)—$R^{12}$ or —$(CH_2)_n$—R, more preferably —$(CH_2)_n$—R.

R is selected from H, a linear or branched alkyl group having 1 to 12 carbon atoms (preferably 6 to 12 carbon atoms), an arylalkyl group having 7 to 12 carbon atoms (preferably phenyl substituted alkyl and most preferably benzyl), —O—$R^{10}$, —O—$R^9$—O—$R^{10}$,

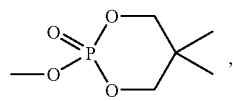

or —Si—$(OR^{11})_3$. In —$(CH_2)_n$—R, n is an integer from 1 to 4, preferably 1. $R^9$ is an alkylene group having 2 to 6 carbon atoms, preferably 2 to 4 carbon atoms. $R^{10}$ is an alkyl group having 1 to 12 carbon atoms, preferably 1 to 8 carbon atoms. $R^{11}$ is an alkyl group having 1 to 8 carbon atoms, preferably 1 to 4 carbon atoms, and more preferably 1 to 2 carbon atoms. $R^{12}$ is selected from a linear or branched alkyl group having 1 to 12 carbon atoms (preferably 6 to 12 carbon atoms), or an arylalkyl group having 7 to 12 carbon atoms (preferably phenyl substituted alkyl and most preferably benzyl).

Examples of suitable epoxides of the invention include, but are not limited to, trimethoxy 2-(7-oxabicyclo [4.1.0] hept-3-yl)ethylsilane ("TMOE"), exo-2,3-epoxynorbornane ("ENB"), 3-benzyloxymethyl-7-oxabicyclo[4.1.0]heptane ("BOCH"), 3-decyloxymethyl-7-oxabicyclo[4.1.0]heptane hereinafter ("DOCH"), 3-n-butoxyethoxymethyl-7-oxabicyclo[4.1.0]heptane ("BEOCH"), 3-(5,5-dimethyl-2-oxo-1,3, 2-dioxaphosphorinanoxymethyl)-7-oxabicyclo[4.1.0] ("DODOH"), 3-(2-ethylhexyloxymethyl)-7-oxabicyclo [4.1.0]heptane ("EOH"), 1-(7-oxabicyclo[4.1.0]hept-3-yl)-1-hexanone ("KHOH"), 1-(7-oxabicyclo[4.1.0]hept-3-yl)-1-phenone ("KPOH"), 4-methyl-3-hexyloxymethyl-7-oxabicyclo[4.1.0]heptane ("MHOCH"), 3-(phenylmethyl)-7-oxabicyclo[4.1.0]heptane ("BOBH"), 5-n-octyloxymethyl-3-oxatricyclo[3.2.1.0$^{2,4}$]octane ("OMOO"), mixtures thereof and the like.

Control epoxide MCS 1562 is 2-ethylhexyl 3,4-epoxycyclohexane-carboxylate, an acid scavenger used in current commercial aircraft hydraulic fluid compositions, described in U.S. Pat. Nos. 3,723,320 and U.S. Pat. No. 5,464,551.

The improved phosphate ester-based functional fluids of the invention containing the epoxides of the invention generate less carboxylic acids during use of the functional fluids while having an acceptable depletion rate during use, such as in a hydraulic system of an aircraft, compared to currently known and used epoxides.

An acid scavenger useful in this invention is trimethoxy 2-(7-(oxabicyclo[4.1.0]hept-3yl)ethylsilane ("TMOE"). This compound is available from Aldrich Company, 1001 West Saint Ave., Milwaukee, Wis. 53233. The chemical structure of TMOE is depicted below.

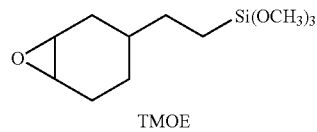

TMOE

Another suitable acid scavenger of the invention is ENB. This compound is available from Aldrich Company, 1001 West Saint Ave., Milwaukee, Wis. 53233. The chemical structure of ENB is depicted below.

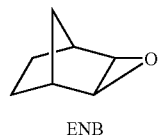

ENB

Another suitable acid scavenger of the invention is BOCH. The chemical structure of BOCH is depicted below.

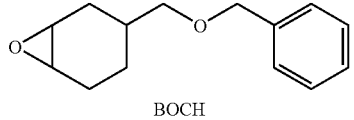

BOCH

Another acid scavenger suitable for use in the invention is DOCH. The chemical structure of DOCH is depicted below.

DOCH

Another suitable acid scavenger of the invention is BEOCH. The chemical structure of BEOCH is depicted below.

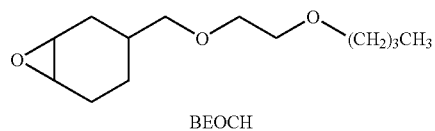

BEOCH

Another compound is useful as an acid scavenger in the invention is DODOH. The chemical structure of DODOH is depicted below.

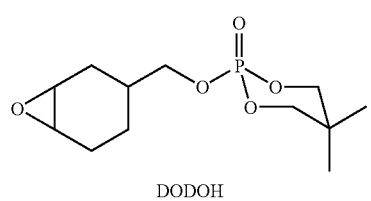

DODOH

Another compound is useful as an acid scavenger in the invention is EOH. The chemical structure of EOH is depicted below.

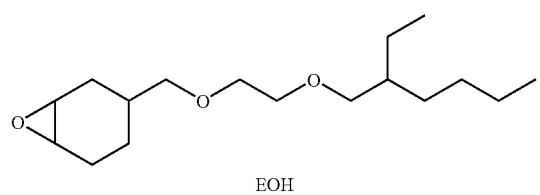

EOH

Another compound is useful as an acid scavenger in the invention is KHOH. The chemical structure of KHOH is depicted below.

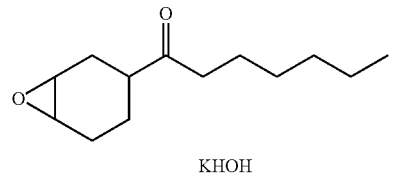

KHOH

Another suitable acid scavenger of the invention is KPOH. The chemical structure of KPOH is depicted below.

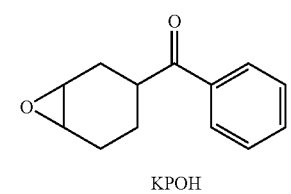

KPOH

Another suitable acid scavenger of the invention is MHOCH. The chemical structure of MHOCH is depicted below.

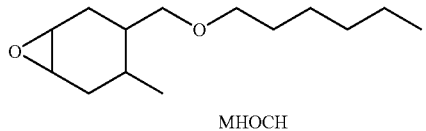

MHOCH

Another suitable acid scavenger of the invention is BOBH. The chemical structure of BOBH is depicted below.

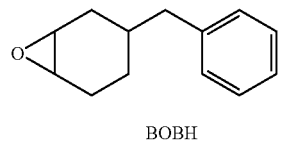

BOBH

Another suitable acid scavenger of the invention is OOMO. The chemical structure of OOMO is depicted below.

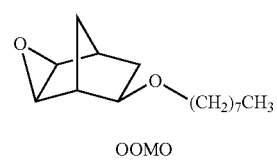

OOMO

The epoxides of the invention are useful when employed in an effective amount with the improved functional fluid, e.g. a hydraulic fluid, using a phosphate ester-based basestock. Typically, an effective amount of epoxide is in the range from about 0.5 to about 20, preferably from about 4 to about 8, percent by weight. In a preferred embodiment, the present invention is directed to an improved functional fluid composition suitable for use as an aircraft hydraulic fluid.

Illustratively, the compounds of this invention may be suitably employed as the acid scavenger(s) in compositions disclosed in U.S. Pat. No. 5,464,551. U.S. Pat. No. 5,464,551 is incorporated herein by reference in its entirety.

An effective acid scavenging amount of the acid scavenger(s) of this invention is typically employed in/with a functional fluid composition. Compounds of this invention may be similarly employed in compositions of U.S. Pat. No. 3,723,320. U.S. Pat. No. 3,723,320 is incorporated herein by reference in its entirety.

The compounds of formula (I) are generally prepared by forming the epoxide from a substituted cyclohexene. The substituted cyclohexene can be prepared from a commercially available material such as cyclohexene-1-methanol by conventional techniques known to those of ordinary skill in the art. Alternatively, the substituted cyclohexene or the precursor to the ultimate substituted cyclohexene can be prepared by the Diels-Alder reaction of a diene, e.g. butadiene or isoprene, with an $\alpha,\beta$-unsaturated carbonyl compound, e.g. 2-butenal, 2-propenal, methyl acrylate, methyl methacrylate, and the like. Optionally, the Diels-Alder reaction product can then be further reacted by conventional techniques known to those of ordinary skill in the art to transform the substitution on the cyclohexene. The epoxide can then be prepared from the desired substituted cyclohexene using conventional techniques known to those of ordinary skill in the art.

One method for preparing an ether-substituted cyclohexene is by conducting a Williamson Synthesis using 3-cyclohexene-1-methanol and a haloalkane or a sulfonate ester. For example, 3-cyclohexene-1-methanol is reacted with a base, e.g. potassium hydroxide, in the presence of dimethylsulfoxide and then further reacted with an alkylchloride. The ether substituted cyclohexene is then converted to the epoxide by conventional techniques using peroxidic reagents, such as m-chloroperoxybenzoic acid, peracetic acid, hydrogen peroxide, sodium hypochloride, and the like.

The compounds of formula (II) are generally prepared by forming the epoxide from a substituted bicyclo[2.2.1]hept-2-ene. The substituted norbornene can be prepared from a material such as 5-norbornene-2-methanol by conventional techniques known to those of ordinary skill in the art. Alternatively, the substituted norbornene or the precursor to the ultimate substituted norbornene can be prepared by the reaction of cyclopentadiene with a readily available 1,1,2,2-substituted olefin. The epoxide can then be prepared from the desired substituted norbornene using conventional techniques known to those of ordinary skill in the art.

An ether-substituted norbornene can be prepared using the same techniques as disclosed above for the ether-substituted cyclohexene.

The synthesis of other substituted cyclohexene or norbornene compounds will be readily apparent to one of ordinary skill in the art based on the above disclosure and the subsequent examples.

The phosphate esters suitable for use in the basestock of the functional fluids of the invention are trialkyl phosphates, triaryl phosphates, dialkyl aryl phosphates, alkyl diaryl phosphates, and mixtures thereof. It is currently preferred that the functional fluid basestock of the invention is a mixture of trialkyl phosphates and triaryl phosphates.

The alkyl subsituents of the phosphate esters of the invention are $C_3$ to $C_8$, preferably $C_4$ to $C_5$. Preferably, the alkyl substituents are selected from n-butyl, isobutyl, n-pentyl or isopentyl, more preferably n-butyl and isobutyl. In the trialkyl phosphates, the three alkyl substituents can be the same or different and mixtures of trialkyl phosphates can be used. Examples of trialkyl phosphates include, but are not limited to, triisobutyl phosphate, tri-n-butyl phosphate, tri(isobutyl/n-butyl) phosphate, tri(isopentyl) phosphate, tri(n-pentyl) phosphate, and mixtures thereof. In the dialkyl aryl phosphates, the two alkyl substituents can be the same or different and mixtures of dialkyl aryl phosphates can be used.

The aryl subsitutents of the phosphate esters of the invention are typically phenyl, but may also be an alkyl-substituted phenyl (alkylphenyl) wherein the alkyl substituent is $C_1$ to $C_9$, preferably $C_3$ to $C_4$. Nonlimiting examples of the alkyl-substituted phenyl substituents include, but are not limited to, tolyl (also known as methylphenyl), ethylphenyl, isopropylphenyl, isobutylphenyl, tert-butylphenyl, and the like. Examples of triaryl phosphates include, but are not limited to, triphenyl phosphate, tri(t-butylphenyl) phosphate, tri(isopropylphenyl) phosphate, tri(isopropylphenyl) phosphate, and mixtures thereof. In the triaryl phosphates and alkyl diaryl phosphates, the aryl substituents can be the same or different and mixtures of alkyl diaryl phosphates and/or triaryl phosphates can be used.

Exemplary phosphate ester basestocks include, but are not limited to, basestocks comprising between about 20% to about 100%, preferably about 50% to about 99%, by weight of trialkyl phosphate, between 0% and about 40%, preferably 0% to about 35%, by weight of dialkyl aryl phosphate, between 0% and about 20%, preferably 0% to about 5%, by weight of alkyl diaryl phosphate, and between 0% and about 20%, preferably 0% to about 10%, by weight of triaryl phosphate.

The functional fluids of the invention optionally contain other components such as antioxidants, viscosity index (VI) improvers, anti-erosion additives, corrosion inhibitors, and anti-foam agents. When the functional fluid is an aircraft hydraulic fluid, the composition preferably further comprises antioxidants, VI improvers, and anti-erosion additives.

To limit the effect of temperature on viscosity, the composition may include a polymeric viscosity index improver. Preferably, the viscosity index improver comprises a poly (alkyl methacrylate) ester of the type described in U.S. Pat. No. 3,718,596. Generally, the viscosity index improver is of high molecular weight, having a number average molecular weight of between about 50,000 and about 100,000 and a weight average molecular weight of between about 200,000 and about 300,000. Preferably, the viscosity index improver of the invention has a relatively narrow range of molecular weight, approximately 95% by weight of the viscosity index improver component having a molecular weight of between about 50,000 and about 1,500,000. The viscosity index improver is present in a proportion sufficient to impart a kinematic viscosity of: at least about 3.0, preferably between about 3 and about 5 centistokes at 210° F.; at least about 9, preferably between about 9 and about 15 centistokes at 100° F.; and not more than about 4200 centistokes at −65° F. Superior shear stability characteristics are also imparted by the viscosity index improver used in the composition. Preferably the functional fluid composition contains between about 3% and about 10% by weight of the viscosity index improver. An example of a particularly preferred viscosity index improver is sold under the trade designation Acryloid® 4495 available from Rohmax USA, Inc. The viscosity index improver is conveniently provided in the form of a solution in a phosphate ester solvent, preferably a trialkyl phosphate ester such as tributyl or triisobutyl phosphate, or a combination of alkyl and phenyl derivatives. The proportions referred to above for the viscosity index improver are on a solids (methacrylate polymer) basis. The phosphate ester solvent becomes in effect part of the basestock, and the ranges of proportions of phosphate esters, as discussed above, reflect the phosphate ester added as a vehicle for the viscosity index improver.

An anti-erosion agent may be incorporated in an amount effective to inhibit flow-induced electrochemical corrosion, more precisely referred to as zeta corrosion. The anti-erosion additive is preferably an alkali metal salt, more preferably a potassium salt of a perfluoroalkylsulfonic acid. Such anti-erosion additives are more fully described in U.S. Pat. No. 3,679,587. Typically, the alkyl component has about 4 to about 12 carbon atoms. Examples of the alkyl component includes, but is not limited to, butyl, hexyl, heptyl, octyl, nonyl, decyl, dodecyl or mixtures thereof, with perfluorooctyl generally affording the best properties. It is particularly preferred that the anti-erosion agent predominantly comprises the potassium salt of perfluorooctylsulfonic acid in a proportion of between about 250 and about 1000 ppm, most preferably at least about 500 ppm.

The composition of the invention may also contain at least one antioxidant additive selected from amine antioxidants, hindered phenols and hindered polyphenols. The antioxidant is preferably a combination of antioxidants selected from amine antioxidants, hindered phenols and hindered polyphenols, more preferably a combination of an amine antioxidant and at least one of a hindered phenol and/or a hindered polyphenol, and most preferably a combination of an amine antiopxidant, a hindered phenol, and a hindered polyphenol. Hydrolytic stability has been found to be improved by partially substituting the hindered polyphenol for the phenol, and it is thus preferred that the composition contain not more than about 1.0%, preferably not more than about 0.7% by weight of a phenol such as a 2,4,6-trialkylphenol. It is generally preferred that the composition contain between about 0.1% and about 0.7% of a 2,4,6-trialkylphenol, preferably 2,6-di-tertiary-butyl-p-cresol [also written as 2,6-di-tert-butyl-p-cresol or 2,6-di-t-butyl-p-cresol ("Ionol")]. The composition preferably further includes between about 0.3% and about 1% of a hindered polyphenol compound, such as a bis(3,5-dialkyl-4-hydroxyaryl) methane, for example, the bis(3,5-di-tert-butyl-4-hydroxyphenyl)methane sold under the trade designation Ethanox® 702 by the Albemarle Corp., a 1,3,5-trialkyl-2,4,6-tris(3,5-dialkyl-4-hydroxyaryl) aromatic compound, for example, the 1,3,5-trimethyl-2,4,6-tris (3,5-di-tert-butyl-4-hydroxyphenyl)benzene sold under the trade designation Ethanox® 330 by the Albemarle Corp., or mixtures thereof. The composition may include an amine antioxidant, preferably a diarylamine such as, for example, phenyl-alpha-napthylamine or alkylphenyl-alpha-naphthylamine, or the reaction product of N-phenylbenzylamine with 2,4,4-trimethylpentene sold under the trade designation Irganox® L-57 by Ciba-Geigy; diphenylamine, ditolylamine, phenyl tolylamine, 4,4'-diaminodiphenylamine, di-p-methoxydiphenylamine, or 4-cyclohexyl-aminodiphenylamine; a carbazole compound such as N-methylcarbazole, N-ethyl-carbazole, or 3-hydroxycarbazole; an aminophenol such a N-butylaminophenol, N-methyl-N-amylaminophenol, or N-isooctyl-p-amino-phenol; an aminodiphenyl-alkane such as aminodiphenylmethanes, 4,4'-diaminodiphenylmethane, etc., aminodiphenylethers; aminodiphenyl thioethers; aryl substituted alkylenediamines such as 1,2-di-o-toluidoethane, 1,2-dianilinoethane, or 1,2-dianilinopropane; aminobiphenyls, such as 5-hydroxy-2-aminobiphenyl, etc.; the reaction product of an aldehyde or ketone with an amine such as the reaction product of acetone and diphenylamine; the reaction product of a complex diarylamine and a ketone or aldehyde; a morpholine such as N-(p-hydroxyphenyl)morpholine, etc.; an amidine such as N,N'-bis-(hydroxyphenyl)acetamidine or the like; an acridan such as 9,9'-dimethyl-acridan, a phenathiazine such as phenathiazine, 3,7-dibutylphenathiazine or 6,6-dioctyl-phenathiazine; a cyclohexylamine; or mixtures thereof. An alkyl substituted diphenylamine such as di(p-octylphenyl) amine is preferred. Certain amine components can also act as a lubricating additive. The amine antioxidant is also preferably present in a proportion of between about 0.3 and about 1% by weight, preferably between about 0.3 and 0.7% by weight, and more preferably between about 0.3 and 0.5% by weight.

The functional fluids of the invention may contain a copper corrosion inhibitor. If a copper corrosion inhibitor is used in the functional fluids of the invention, the copper corrosion inhibitor preferably includes a benzotriazole derivative, such as that sold under the trade designation Petrolite 57068. This corrosion inhibitor is present in an amount sufficient to deactivate metal surfaces in contact with the fluid composition against the formation of metal oxides on the metal surfaces in contact with the fluid, thereby reducing rates of copper dissolution into the hydraulic fluid, and also reducing dissolution of perhaps parts fabricated from copper alloys. Advantageously, the functional fluids of the invention contains between about 0.005% and about 0.09% by weight of the benzotriazole derivative, preferably between about 0.02 and about 0.07% by weight.

Phosphate ester functional fluids are known to corrode iron alloys as well as copper alloys. Numerous iron corrosion inhibitors are available for use in functional fluids, but these are known in many instances to increase rates of erosion and thus have a net deleterious effect on the performance properties of the hydraulic fluid. However, certain 4,5-dihydroimidazole compounds are effective iron corrosion inhibitors that do not adversely affect the erosion properties of the fluid. Useful 4,5-dihydroimidazole compounds include those that correspond to the structural formula

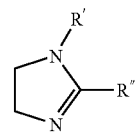

where R' is hydrogen, alkyl alkenyl, hydroxyalkyl, hydroxyalkenyl, alkoxyalkyl or alkoxyalkenyl, and R" is alkyl, alkenyl or an aliphatic carboxylate. Exemplary groups that may constitute R' include hydrogen, methyl, ethyl, propyl, butyl, pentyl, octyl, vinyl, propenyl, octenyl, hexenyl, hydroxyethyl, hydroxyhexyl, methoxypropyl, propoxyethyl, butoxypropenyl, etc. Exemplary group, which may constitute R" include, octyl, dodecyl, hexadecyl, heptadecenyl, or a fatty acid substituent such as 8-carboxy-octyl, 12-carboxydodecyl, 16-carboxyhexadecenyl, or 18-carboxyoctadecyl. In a particularly effective embodiment, R∝ is hydrogen or lower alkyl and R" is a fatty acid residue containing at least about 9 carbon atoms, i.e., —$C_8$—COOH to —$C_{18}$COOH, preferably $C_{16}$—COOH to $C_{18}$—COOH. In another preferred embodiment, R' is a lower hydroxyalkyl and R" is a $C_8$–$C_{18}$ alkenyl. In the latter instance, however, the most satisfactory inhibition of Fe corrosion is realized only if the 4,5-dihydro-imidazole is used in combination with an amino acid derivative, more particularly an N-substituted amino acid in which the N-substituent contains both polar and oleophilic moieties, for example, an N-alkyl-N-oxo-alkenyl amino acid.

A suitable iron corrosion inhibitor is the condensation product of 4,5-dihydro-1H-imidazole and $C_{16}$–$C_{18}$ fatty acid (sold under the trade designation Vanlube RI-G by the Vanderbilt Co.). Also effective as a 4,5-dihydroimidazole compound is 2-(8-heptadecenyl)-4,5-dihydro-1H-imidazole-1-ethanol (sold under the trade designation Amine-O by Ciba-Geigy). To function as an iron corrosion inhibitor, the latter compound should be used in combination with an amino acid derivative such as, e.g., the N-methyl-N-(1-oxo-9-octadecenyl)glycine sold under the trade designation Sarkosyl®-O by Ciba-Geigy Corporation.

Other iron corrosion inhibitors have been found effective in the functional fluids of the invention without adverse effect on erosion characteristics. Acceptable iron corrosion inhibitors include, for example, the product sold by Petrolite under the trade designation Petrolite P-31001.

As necessary, the functional fluids of the invention may also contain an anti-foaming agent. Preferably, this is a silicone fluid, more preferably a polyalkylsiloxane, for example, the polymethylsiloxane sold under the trade designation DC 200 by Dow Corning. Preferably the anti-foam agent is included in a proportion sufficient to inhibit foam formation under the test conditions of ASTM method 892. Typically, the anti-foam content of the composition is at least about 0.0005% by weight, typically about 0.0001% to about 0.001% by weight.

Preferably, the pH of the functional fluids of the invention is at least about 7.5, more preferably between about 7.5 and about 9.0. To impart a pH in this range and to enhance the acid scavenging capacity of the formulation, the functional fluids may further include between about 0.0035 and about 0.10%, preferably between about 0.01% and about 0.1% by weight, most preferably between about 0.02% and about 0.07% of an alkali metal phenate or other arenate. Potassium phenate is preferred. In addition to neutralizing acidic components of the composition, the alkali metal arenate serves to pacify the metal surfaces when the composition has been added to a hydraulic system, thereby reducing corrosion.

A second embodiment of the invention relates to a method for reducing the production of carboxylic acid during use of a functional fluid comprising (a) a basestock comprising a phosphate ester, and (b) at least one acid scavenger, the method comprising admixing in the functional fluid at least one acid scavenger selected from epoxides of the invention as described herein.

EXAMPLES

The following specific examples illustrate the best currently-known mode of making and using the invention and are provided merely to facilitate a clear understanding of the invention. It should be understood, however, that the detailed expositions of the application of the invention, while indicating preferred embodiments, are given by way of illustration only and are not to be construed as limiting the invention since various changes and modifications within the spirit and scope of the invention will become apparent to those skilled in the art from this detailed description.

Several epoxides of this invention were prepared as shown below to illustrate the invention. Two commercially available epoxides include TMOE and ENB, which were purchased from Aldrich Company, 1001, West Saint Ave, Milwaukee, Wis., 53233 USA. All other starting materials were purchased from Aldrich Company and used as received.

Gas chromatography-FID ("GC") was performed on a HP 5890 fitted with a 25 m ×0.32 mm HP-5 capillary column interfaced with a HP 5890A controller. The GC program used was: initial temperature: 50° C., initial time: 3 min., program rate: 8° C./min., final temperature: 280° C., final time: 5 min.

Gas chromatography mass spectra (EI), ("GC/MS"), was obtained on a HP 5970 mass detector coupled to a HP 5890 gas chromatograph fitted with a 25 m ×0.32 mm HP capillary column with a 5970 series mass selective detector at an ionization voltage of 70 eV and interfaced with a HP 5890A controller. For the determination of low molecular weight volatile compounds—GC program used was: initial temperature: 50° C., initial time: 5 min., program rate: 20° C./min., final temperature: 280° C., final time: 5 min. For the determination of high molecular weight compounds—GC program used was: initial temperature: 50° C., initial time: 3 min., program rate: 8° C./min., final temperature: 280° C., final time: 5 min. Liquid chromatography mass spectra ("LC/MS") was obtained by directly infusing the sample into a Finnigan LCQ ion trap mass spectrometer with an Atmospheric Pressure Chemical Ionization (APCI) interface. Molecular weights (Mw) were determined using either the GC/MS or the LC/MS method.

NMR was run on a SUN-based Varian 300 MHz NMR spectrometer. Except as noted, NMR spectra were obtained as chloroform-d ($CDCl_3$) solutions with TMS as the internal standard. Chemical shifts are reported in parts per million (ppm) downfield from TMS.

Example 1

Preparation of EOH

A. Synthesis of 2-ethylhexyl tosylate.

A 500 mL round bottom flask equipped with a stirrer bar was charged with 78 g (0.60 mol) 2-ethyl hexyl alcohol and 170 mL of pyridine. The mixture was cooled to 0° C. Tosyl chloride (120.8 g, 0.63 mol) was slowly added to the above mixture at 0-5° C. The reaction was carried out for 3 hrs. The reaction mixture was poured into 1.2 L of HCl solution (1 M), extracted with chloroform (3×200 mL), washed with water (3×200 mL) and dried with sodium sulfate. The organic layer was evaporated and the residue vacuum distilled to give a 2-ethylhexyl tosylate.

B. Synthesis of 3-(2-Ethylhexoxymethyl)cyclohexene

A 500 mL round bottom flask equipped with a mechanical stirrer was charged with 33.6g (0.30 mol) cyclohexene-1-methanol, and 260 mL of DMSO. Sodium hydride (8.43 g, 95% in purity; 0.334 mol) was slowly added to above mixture in ice bath over 40 min. After the above mixture was reacted at room temperature for 2 hrs, the reaction mixture was warmed to room temperature. 2-Ethylhexyl tosylate (85.2 g, 0.30 mol) was slowly added to the above mixture over 15 min. The reaction was carried out for another 1 hr at room temperature, then 60° C. for 2 hrs. The reaction mixture was added to water (200 mL), and then extracted with chloroform (3×180 mL), washed with water (2×100 mL). The organic layer was evaporated and the residue distilled to give pure product.

C. Synthesis of 3-(2-ethylhexoxymethyl)-7-oxabicyclo[4.1.0]heptane

A 500 mL round bottom flask equipped with a stirrer bar was charged with 22.4g (0.10 mol) 3-(2-ethylhexoxymethyl) cyclohexene, and 50 mL of methylene chloride. m-Chloroperbenzoic acid (28.3 g, 85% in purity; 0.138 mol) in methylene chloride (200 mL) was added dropwise to above mixture over 1 hr in an ice bath. After the above mixture was reacted at room temperature overnight, the reaction mixture was filtered. The solid was washed with hexane (3×30 mL). The precipitate was filtered, 50 mL of hexane was added into filtrate to further precipate m-chlorobenzoic acid. The solid was filtered and washed with hexane (2×20 mL). The solvent was evaporated and the residue distilled to give pure product.

$^1$H NMR (CDCl$_3$): 3.18 (d, 2H), 3.07 (d, 2H), 3.13 (t, 1H), 3.08 (t, 2H), 2.09 (m, 2H), 1.67 (m, 2H), 1.41 (m, 1H), 1.40 (m, 1H), 1.37–0.90 (m, 8H), 0.82 (t, 3H), 0.80 (t, 3H).

$^{13}$C NMR (d-acetone): 11.4, 14.5, 21.7, 23.4, 23.4, 24.2, 24.2, 24.3, 25.1, 27.9, 27.9, 28.7, 29.4, 30.3, 30.9, 30.9, 33.4, 39.9, 33.9, 51.7, 52.2, 52.9, 53.4, 74.0, 74.2, 75.7, 76.2.

Mw=240.

Example 2

Preparation of BOCH

A. Synthesis of 3-benzoxymethylcyclohexene

A 500 mL round bottom flask equipped with a mechanical stirrer was charged with 19.8 g (0.177 mol) cyclohexene-1-methanol, and 150 mL of DMSO. Sodium hydride (4.90 g, 95% in purity; 0.194 mol) was slowly added to above mixture in an ice bath over 20 min. After the above mixture was reacted at room temperature for 1 hr, 30.2 g (0.177 mol) of benzylbromide was slowly added to the above mixture over 15 min. The reaction was carried out at 60° C. for 2 hrs. The reaction mixture was cooled to room temperature and was added to water (200 mL), and then extracted with chloroform (3×200 mL), washed with water (2×250 mL) and dried with sodium sulfate. The solvent was evaporated and the residue distilled to give pure product.

$^1$H NMR (CDCl$_3$): 7.28 (5H, Ph), 5.56 (2H, CH$_2$Ph), 4.50 (2H, 2CH), 3.37 (2H, CH$_2$O ), 1.68–2.20 (7H, ring CH$_2$, CH), 1.30 (2H, ring CH$_2$, CH), 130 (2H, ring CH$_2$).

$^{13}$C NMR (CDCl$_3$): 138.7, 128.2, 127.4, 127.4, 127.0, 126.0, 75.2, 72.9, 33.9, 28.5, 25.6, 24.5.

B. Synthesis of 3-benzoxymethyl-7-oxabicyclo[4.1.0]heptane

A 500 mL round bottom flask equipped with a stirring bar was charged with 13.1g (0.065 mol) 3-benzoxymethylcyclohexene, and 100 mL of methylene chloride. Peracetic acid (15.5 g, 35 wt. % in acetic acid; 0.065 mol) in methylene chloride (80 mL) was added dropwise to the above mixture over 30 min. in an ice bath. After the above mixture was reacted at room temperature for 24 hrs, 250 mL of water was added to the above reaction mixture, the water layer was extracted with methylene chloride (2×150 mL), the organic layer was combined, and washed with saturated sodium carbonate solution (2×150 mL), then with water (2×150 mL) and dried with sodium sulfate. The solvent was evaporated and the residue distilled to give pure product.

$^1$H NMR (CDCl$_3$): 7.28 (5H, Ph), 4.45 (2H, CH$_2$Ph), 3.23 (2H, 2CHO), 3.26 (2H, PhCH$_2$O), 3.11 (2H, CH$_2$O ), 1.28–3.10(6H, ring CH$_2$), 0.8–1.21 (1H, ring CH).

$^{13}$C NMR (CDCl$_3$): 138.4, 138.3, 128.1, 127.3, 127.2, 75.0, 74.5, 72.8, 72.6, 52.5, 52.3, 51.6, 51.1, 32.9, 29.9, 28.1, 27.3, 24.5, 23.7, 22.8, 21.1.

Mw=218.

Example 3

Preparation of DOCH

A. Synthesis of 3-cyclohexene-1-methanol tosylate.

A 500 mL round bottom flask equipped with a stirring bar was charged with 67.2 g (0.60 mol) 3-cyclohexene-1-methanol, and 170 mL of pyridine. The mixture was cooled to 0° C. Tosyl chloride (120.8 g, 0.63 mol) was slowly added to above mixture at 0–5° C. The reaction was carried out for 3 hrs. The reaction mixture was poured into 1.2 L of HCl solution (1 M), extracted with chloroform (3×200 mL), washed with water (3×200 mL), dried with sodium sulfate. The solvent was evaporated and the residue distilled under vacuum to give a tosylate.

B. Synthesis of 3-decyloxymethylcyclohexene

A 500 mL round bottom flask equipped with a mechanical stirrer was charged with 23.7g (0.15 mol) decyl alcohol, and 150 mL of DMSO. Sodium hydride (4.22 g, 95% in purity; 0.167 mol) was slowly added to above mixture in an ice bath over 20 min. After the above mixture was reacted at room temperature for 3 hrs, the reaction mixture was cooled to room temperature. 3-Cyclohexene-1-methanol tosylate (39.9 g, 0.15 mol) was slowly added to the above mixture over 20 min. The reaction was carried at room temperature overnight, then 80° C. for 3 hrs. The reaction mixture was added to water (150 mL), and then extracted with chloroform (3×150 niL), washed to water (2×100 mL) and dried with sodium sulfate. The solvent was evaporated and the residue distilled to give pure product.

C. Synthesis of 3-decyloxymethyl-7-oxabicyclo[4.1.0]heptane

A 500 mL round bottom flask equipped with a stirring bar was charged with 16.4g (0.065 mol) 3-decyloxymethylcyclohexene, and 100 mL of methylene chloride. Peracetic acid (15.5 g, 35 wt. % in acetic acid; 0.065 mol) in methylene chloride (80 mL) was added dropwise to above mixture over 30 min. in an ice bath. After the above mixture was reacted at room temperature overnight, 250 mL of water was added to above reaction mixture, the water layer was extracted with methylene chloride (2×150 mL), the organic layer was combined, and washed with saturated sodium carbonate solution (2×150 mL), then with water (2×150 mL) and dried with sodium sulfate. The solvent was evaporated and the residue distilled to give pure product.

$^1$H NMR (CDCl$_3$): 3.34(2H, OCH$_2$), 3.18 (2H, 2CHO), 3.12 (2H, CH$_2$O), 2.10 (2H, ring CH$_2$), 1.80 (2H, ring CH$_2$), 1.52 (2H, ring CH$_2$), 1.42 (1H, ring CH), 1.27 (16H, 8 CH$_2$), 0.87 (3H, CH$_3$).

$^{13}$C NMR (CDCl$_3$): 75.6, 75.1, 71.0, 70.9, 52.5, 52.4, 51.6, 51.1, 33.0, 31.7, 29.9, 29.5, 29.5, 29.5, 29.4, 29.3, 29.2, 28.2, 27.5, 26.0, 24.6, 23.8, 22.9, 22.5, 21.2, 13.9.

Mw=268.

Example 4

Preparation of BEOCH

A. Synthesis of 3-butoxyethoxymethylcyclohexene

A 500 niL round bottom flask equipped with a mechanical stirrer was charged with 16.7g (0.15 mol) 2-butoxyethanol, and 150 mL of DMSO. Sodium hydride (4.22 g, 95% in purity; 0.167 mol) was slowly added to above mixture in an ice bath over 20 min. After the above mixture was reacted at room temperature for 3 hrs, 39.9 g (0.15 mol) of 3-cyclohexene-1-methanol tosylate was slowly added to the above mixture over 20 min. The reaction was carried at room temperature overnight, then 80° C. for 3 hrs. The reaction mixture was added to water (150 mL), and then extracted with chloroform (3×150 mL), washed with water (2×100 mL), dried with sodium sulfate. The solvent was evaporated and the residue distilled to give pure product.

$^1$H NMR (CDCl$_3$): 5.64 (2H, 2CH), 3.58(4H, 2OCH$_2$), 3.47 (2H, OCH$_2$), 3.35 (2H, CH$_2$O), 1.70–2.26 (7H, ring CH, 3CH$_2$), 1.56 (2H, CH$_2$), 1.36 (2H, CH$_2$), 1.24 (2H, ring CH$_2$), 0.92 (3H, CH$_3$).

$^{13}$C NMR (CDCl$_3$): 126.9, 125.9, 76.2, 71.1, 70.3, 70.0, 33.6, 31.6, 28.4, 25.5, 24.4, 19.2, 13.8.

B. Synthesis of 3-butoxyethoxymethyl-7-oxabicyclo[4.1.0]heptane

A 500 mL round bottom flask equipped with a stirrer bar was charged with 13.78 g (0.065 mol) 3-butoxyethoxymethylcyclohexene, and 100 niL of methylene chloride. Peracetic acid (15.5 g, 35 wt. % in acetic acid; 0.065 mol) in methylene chloride (80 mL) was added dropwise to above mixture over 30 min. in an ice bath. After the above mixture was reacted at room temperature overnight, 250 mL of water was added to above reaction mixture, the water layer was extracted with methylene chloride (2×150 mL), the organic layer was combined, and washed with saturated sodium carbonate solution (2×150 mL), then with water (2×150 mL) and dried with sodium sulfate. The solvent was evaporated and the residue distilled to give pure product.

$^1$H NMR (CDCl$_3$): 3.55(4H, 2OCH$_2$), 3.46 (2H, OCH$_2$), 3.20–3.34 (2H, 2CHO), 3.14 (2H, CH$_2$O), 1.66–2.20 (7H, ring CH, 3CH$_2$), 1.56 (2H, CH$_2$), 1.36 (2H, CH$_2$), 0.96–1.20 (2H, ring CH$_2$), 0.92 (3H, CH$_3$).

$^{13}$C NMR (CDCl$_3$): 75.8, 75.4, 70.7, 70.0, 69.9, 69.7, 69.6, 52.1, 52.0, 51.3, 50.8, 32.6, 31.4, 29.5, 27.9, 27.1, 24.3, 23.5, 22.6, 20.9, 18.9, 13.5.

Mw=228.

Example 5

Preparation of DODOH

A. Synthesis of 3-(5,5-dimethyl-2-oxo-1,3,2-dioxaphosphorinanoxymethyl)-cyclohexene.

A 100 mL round bottom flask equipped with a stirrer bar was charged with 15.04 g (0.134 mol) 3-cyclohexene-1-methanol, 22.52 g (0.122 mol) of 2-chloro-5,5-dimethyl-1,3,2-dioxaphosphorinan-2-one, and 10.6 g (0.134 mol) of pyridine. After the above mixture was reacted at 80° C. for 3 hrs. The reaction mixture was added to chloroform (100 mL), and then washed with chloroform (2×100 mL), dried with sodium sulfate. The solvent was evaporated and the residue distilled to give pure product.

$^1$H NMR (CDCl$_3$): 5.68 (2H, 2CH), 3.87–4.12 (6H, 3OCH$_2$), 1.76 –2.02 (4H, 2 ring CH$_2$), 1.74–1.88 (2H, ring CH$_2$), 1.28–1.43 (1H, ring CH), 1.25 (3H, CH$_3$), 0.91 (3H, CH$_3$)

$^{13}$C NMR (CDCl$_3$): 126.2, 124.4, 77.0, 70.9, 70.6, 70.5, 33.5, 33.4, 33.4, 33.3, 26.9, 24.0, 23.4, 20.7, 19.5.

B. Synthesis of 3-(5,5-dimethyl-2-oxo-1, 3, 2-dioxaphosphorinanoxymethyl)-7-oxabicyclo[4. 1.0]heptane.

A 500 mL round bottom flask equipped with a stirrer bar was charged with 15.5 g (0.058 mol) 3-(5,5-dimethyl-2-oxo-1,3,2-dioxaphosphorinanoxymethyl)-1-cyclohexene, and 100 mL of methylene chloride. Peracetic acid (13.76 g, 35 wt. % in acetic acid; 0.058 mol) in methylene chloride (60 mL) was added dropwise to above mixture over 20 min. in an ice bath. After the above mixture was reacted at room temperature overnight, 100 mL of water was added to above reaction mixture, the water layer was extracted with methylene chloride (2×100 mL), the organic layer was combined, and washed with saturated sodium carbonate solution (2×100 mL), then with water (2×100 mL), dried with sodium sulfate. The solvent was evaporated and the residue distilled to give pure product.

$^1$H NMR (CDCl$_3$): 4.07 (1H, CHO), 4.03 (1H, CHO), 3.82–4.00 (4H, 2OCH$_2$), 3.19 (2H, OCH2), 2.10 (2H, ring CH$_2$), 1.80 (2H, ring CH$_2$), 1.57 (2H, ring CH$_2$), 1.24 (3H, CH$_3$), 1.08 (1H, ring CH), 0.90 (3H, CH$_3$).

$^{13}$C NMR (CDCl$_3$): 77.4, 77.3, 70.8, 52.0, 51.2, 50.5, 33.1, 33.0, 31.8, 31.7, 30.5, 30.4, 27.4, 26.3, 24.0, 22.9, 22.4, 21.2, 21.1, 20.3, 20.0.

Mw=276.

Example 6

Preparation of KHOH

A. Synthesis of 1-(3-cyclohexen-1-yl)-1-hexanone

A 500 mL round bottom flask equipped with a mechanical stirrer was charged with 18.9 g (0.15 mol) 3-cyclohexene-1-carboxylic acid, and 300 mL of ether. 132 mL of hexylithium (2.5 M solution in hexane, 0.33 mol) was slowly added to above mixture in ice bath over 40 min. After the above mixture was reacted at 0° C. for 30 minutes, the reaction mixture was warmed to room temperature. The mixture is slowly added into a vigorously stirred mixture of 27 mL (0.32 mol) of concentrated HCl and 400 mL of water. The organic phase is separated, and aqueous phase is extracted with 3×150 mL of ether, the combined organic solution is dried over sodium sulfate, and the solution is evaporated and distilled to give pure product.

B. Synthesis of 1-(7-oxabicyclo[4.1.0]hept-3-yl)-1-hexanone

A 500 mL round bottom flask equipped with a stirrer bar was charged with 8.42 g (0.0668 mol) 1-(3-cyclohexen-1-yl)-1-hexanone, and 80 mL of methylene chloride. Peracetic acid (14.5 g, 35 wt. % in acetic acid; 0.0668 mol) in methylene chloride (60 mL) was added dropwise to above mixture over 20 min. in an ice bath. After the above mixture was reacted at room temperature overnight, 200 mL of water was added to above reaction mixture, the water layer was extracted with methylene chloride (2×100 mL), the organic layer was combined, and washed with saturated sodium carbonate solution (2×100 mL), then with water (2×100 mL), dried with sodium sulfate. The solvent was evaporated and the residue distilled to give pure product.

¹H NMR (CDCl₃): 3.20 (2H, 2CHO), 2.60 (1H, CH), 2.40 (2H, CH₂), 1.60–2.36 (9H, CH, 4CH₂), 1.28 (8H, 4CH₂), 0.88 (3H, CH₃).

¹³C NMR (d-acetone): 213.1, 212.7, 52.4, 51.7, 51.3, 50.6, 45.1, 42.5, 40.7, 40.3, 31.4, 28.7, 26.4, 25.3, 24.2, 23.5, 23.4, 22.8, 22.4, 22.3, 20.6, 13.8.

Mw=210.

Example 7

Preparation of KPOH

A. Synthesis of 3-cyclohexen-1-yl phenone

A 500 mL round bottom flask equipped with a mechanical stirrer was charged with 18.9 g (0.15 mol) 3-cyclohexene-1-carboxylic acid, and 300 mL of ether. Phenyllithium (183 mL, 1.8 M solution in hexane, 0.33 mol) was slowly added to above mixture in an ice bath over 50 min. After the above mixture was reacted at 0° C. for 40 minutes, the reaction mixture was warmed to room temperature. The mixture is slowly added into a vigorously stirred mixture of 27 mL (0.32 mol) of concentrated HCl and 400 mL of water. The organic phase is separated, and aqueous phase is extracted with 3×150 mL of ether, the combined organic solution is dried over sodium sulfate, and the solution is evaporated and distilled to give pure product.

B. Synthesis of 1-(7-oxabicyclo[4.1.0]hept-3-yl)-1-phenone

A 500 mL round bottom flask equipped with a stirrer bar was charged with 8.45 g (0.0454 mol) 3-cyclohexen-1-yl phenone and 80 mL of methylene chloride. Peracetic acid (12.0 g, 35 wt. % in acetic acid; 0.0503 mol) in methylene chloride (60 mL) was added dropwise to above mixture over 25 min. in an ice bath. After the above mixture was reacted at room temperature overnight, 200 mL of water was added to above reaction mixture, the water layer was extracted with methylene chloride (2×100 mL), the organic layer was combined, and washed with saturated sodium carbonate solution (2×100 mL), then with water (2×100 mL), dried with sodium sulfate. The solvent was evaporated and the residue distilled to give pure product.

¹H NMR (CDCl₃): 7.85–7.38 (5h, Ph), 3.52–3.10 (3H, 2CHO, 1CH), 2.24–1.22 (6H, 3CH₂).

¹³C NMR (d-acetone): 202.6, 201.4, 135.8, 135.6, 132.8, 132.7, 128.5, 128.1, 127.9, 52.6, 52.4, 51.7, 51.5, 50.8, 50.6, 40.2, 37.6, 27.2, 26.0, 24.6, 23.4, 22.7, 21.8.

Mw=202.

Example 8

Preparation of MHOCH

A. Synthesis of 6-methyl-3-hexoxymethylcyclohexene

A 500 mL round bottom flask equipped with a mechanical stirrer was charged with 18.9g (0.15 mol) 6-methyl-3-cyclohexenemethanol, and 130 mL of DMSO. Sodium hydride (4.22 g, 95% in purity; 0.167 mol) was slowly added to above mixture in ice bath over 25 min. After the above mixture was reacted at room temperature for 2 hrs. Hexyl bromide (27.3 g, 0.165 mol) was slowly added to the above mixture over 25 min. The reaction was carried at room temperature for 1 hr, then 70° C overnight. The reaction mixture was added to water (150 mL), and then extracted with chloroform (3×150 mL), washed with water (2×150 mL), dried with sodium sulfate. The solvent was evaporated and the residue distilled to give pure product.

B. Synthesis of 4-methyl-3-hexoxymnethyl-7-oxabicyclo[4.1.0]heptane

A 500 mL round bottom flask equipped with a stirrer bar was charged with 10.86g (0.052 mol) of 5-methyl-4-hexoxymethylcyclohexene, and 80 mL of methylene chloride. Peracetic acid (12.3 g, 35 wt. % in acetic acid; 0.052 mol) in methylene chloride (60 mL) was added dropwise to above mixture over 15 min. in an ice bath. After the above mixture was reacted at room temperature overnight, 200 mL of water was added to above reaction mixture, the water layer was extracted with methylene chloride (2×150 mL), the organic layer was combined, and washed with saturated sodium carbonate solution (2×150 mL), then with water (2×150 mL), dried with sodium sulfate. The solvent was evaporated and the residue distilled to give pure product.

¹H NMR (CDCl₃): 3.42–3.24 (4H, 2OCH₂), 3.14 (2H, 2CHO), 2.22–1.40 (6H, 2CH, 2CH₂), 1.30 (8H, 4 CH₂), 10.86 (6H, 2CH₃).

¹³C NMR (CDCl₃): 73.0, 72.4, 71.7, 71.0, 53.1, 52.6, 51.8, 51.6, 39.1, 35.8, 34.3, 33.3, 33.1, 31.5, 31.0, 29.5, 29.3, 29.1, 28.0, 26.4, 25.7, 25.3, 24.4, 22.5, 18.9, 16.7, 15.4, 13.9.

Mw=226.

Example 9

Preparation of BOBH

A. Synthesis of (3-cyclohexen-1-ylmethyl)benzene

A 500 nL round bottom flask equipped with a mechanical stirrer was charged with 100 mL of diethylene glycol and 15.6 g (0.18 mol, 85% in purity) of KOH. The mixture was heated to 120° C. until the KOH began to melt and go into solution. After the solution had been cooled to 85° C., 14.88 g (0.08 mol) of 3-cyclohexen-1-yl phenone was slowly added to the above mixture. The mixture was slowly heated to reflux for 2.5 hrs., then was cooled to room temperature. The reaction mixture was extracted with 3×80 mL of ether, the combined organic solution was dried over sodium sulfate, and the solution was evaporated and the residue was vacuum distilled to give pure product.

¹H NMR (CDCl₃); 7.11–7.31 (5H, Ph), 5.63 (2H, 2CH), 2.55 (2H, PhCH₂), 2.01 (3H, CH₂, CH), 1.84 (1HH, CH), 1.72 (2H, CH₂), 1.27 (1H, CH).

¹³C NMR (CDCl₃): 140.8, 129.0, 128.0, 126.8, 126.2, 125.5, 43.1, 35.6, 31.7, 28.5, 25.2.

B. Synthesis of 3-(phenylmethyl)-7-oxabicyclo[4.1.0]heptane

A 500 mL round bottom flask equipped with a stirrer bar was charged with 9.55 g (0.056 mol) of (3-cyclohexen-1-ylmethyl)benzene, and 90 mL of methylene choride. Peracetic acid (17.5 g, 35 wt. % in acetic acid; 0.073 mol) in methylene chloride (70 mL) was added dropwise to the above mixture over 25 min. in an ice bath. After the above mixture was reacted at room temperature for 7 hrs., 200 mL of water was added to the above reaction mixture, the water layer was extracted with chloroform (2×150 mL). The organic layer was combined, washed with saturated sodium carbonate solution (2×150 mL), then with water (2×150 mL), and dried with sodium sulfate. The solvent was evaporated and the residue was vacuum distilled to give pure product.

¹H NMR (d-choloroform): 7.05–7.29 (5h, Ph), 3.07 (2H, 2CHO), 2.43 (2H, PhCH), 0.8–2.45 (7H, CH and 3CH₂).

$^{13}$C NMR (d-choloroform): 140.1, 140.0, 128.9, 128.9, 127.9, 127.9, 125.6, 53.0, 52.4, 51.6, 51.5, 43.2, 42.6, 34.7, 31.6, 31.4, 30.6, 26.7, 25.1, 24.1, 23.4.

Mw=188.

Example 10

Preparation of OMOO

A. Synthesis of 4-n-octyloxymethylbicyclo[2.2.1]hept-2-ene

A 500 mL round bottom flask equipped with a mechanical stirrer was charged with 9.7g (0.075 mol) of 5-norbornene-2-methanol, and 25 ml of DMSO. Potassium hydroxide (7.3g, 85% in purity; 0.13 mol) was added to the above mixture. After the above mixture was reacted at room temperature for 4 hrs., 15.9 g (0.15 mol) of n-octylbromide was slowly added to the above mixture over 25 min. The reaction was carried out at 80° C. for 3.3. hrs. After the reaction mixture was cooled to room temperature, the reaction mixture was combined with water (100 mL), extracted with chloroform (2×150 mL), washed with water (2×100 mL), and dried with sodium sulfate. The solvent was evaporated and the residue was vacuum distilled to give pure product.

$^1$H NMR (major isomer, CDCl$_3$); 6.12 (1H, =CH), 5.91 (1H, =CH), 3.35 (2H. OCH$_2$), 3.12 (1H, OCH), 2.98 (1H, CHO). 2.78 (1H, ring CH), 2.77 (1H, ring CH), 2.32 (1H, ring CH), 1.78 (1H, ring CH), 1.53 (3H, ring CH, CH$_2$), 1.36 (12H, 6CH$_2$), 0.88 (3H, CH$_3$).

$^{13}$C NMR (CDCl$_3$): 136.9, 136.6., 136.5, 132.5, 75.5, 74.6, 71.1., 71.0, 49.3, 44.9, 43.9, 43.6, 42.1, 41.5, 38.8, 38.8, 31.8, 29.7, 29.4, 29.3, 29.1, 26.2, 22.6., 14.0.

B. Synthesis of 5-n-octyloxymethyl-3-oxatricyclo[3.2.1.0$^{2,4}$]octane

A 500 mL round bottom flask equipped with a stirrer bar was charged with 14.3 g (0.056 mol) of 4-n-octyloxymethyl-bicyclo[2.2.1]hept-2-ene, and 80 mL of methylene choride. Peracetic acid (15.6 g, 35 wt. % in acetic acid; 0.072 mol) in methylene chloride (70 mL) was added dropwise to the above mixture over 20 min. in an ice bath. After the above mixture was reacted at room termperature for 3 hrs., 100 mL of water was added to the above reaction mixture, the organic layer was washed with saturated sodium carbonate solution (2×100 mL), then with water (2×100 mL), and dried with sodium sulfate. The solvent was evaporated and the residue was vacuum distilled to give pure product.

$^1$H NMR (CDCl$_3$): 3.32–3.48 (3H, 3OCH), 3.08–3.26 (3H, 3OCH), 2.44 (2H, CH$_2$), 1.76 (2H, ring CH$_2$), 1.58 (3H, CH, CH$_2$), 1.28 (12H, 6CH$_2$), 0.88 (3H, CH$_3$).

$^{13}$C NMR (CDCl$_3$): 73.5, 71.6, 71.2, 51.9, 51.5, 51.2, 49.6, 40.9, 39.1, 38.3, 38.2, 37.1, 36.8, 31.8, 30.1, 29.7, 29.6, 29.5, 29.3, 28.8., 27.2, 26.2, 26.1, 23.3, 22.7, 14.2.

Mw=252.

Example 11

Kinetic Study Procedure

Epoxide (0.01 mol) was added into 50 g of tributylphosphate (containing 0.3 wt. % water). Naphthalene (1 wt. %) was added into above mixture as a GC internal standard. The sample was then sealed into glass tubes and put into a 163° C. oven. The sample was taken after selected time intervals. After the sample was cooled to room temperature, the sample was analyzed by GC. The remaining epoxide % was calculated by the following equation:

Remaining expoxide $\%=((Ax/Aix))\times((Aio/Ao))$ where

Ax, Aix: epoxide and internal standard area at given time

Aio, Ao, initial internal standard and epoxide area (without heating).

Data:

The following data (remaining epoxide % v. time) was obtained using the Kinetic Study Procedure described above. The data comparing the epoxide depletion of the epoxides of the invention with control MCS-1562 was plotted in FIG's. 1–7. The epoxides of the invention all result in functional fluids having a reduced production of carboxylic acid during use of the functional fluid while maintaining an acceptable epoxide depletion rate.

TABLE 1

| C Time (Hrs) | MCS1562 | EOH |
| --- | --- | --- |
| 0.0 | 100% | 100% |
| 24.0 | 84.0% | 85.0% |
| 51.0 | 70.0% | 74.0% |
| 72.0 | 47.0% | 59.0% |
| 144.0 | 30.0% | 26.0% |
| 264 | 0% | 1.3% |
| 336 | 0% | 0% |

TABLE 2

| Time (hr) | MCS1562 | ENB | TMOE |
| --- | --- | --- | --- |
| 0 | 100% | 100% | 100% |
| 24 | 84.00% | 38.40% | 11.40% |
| 51 | 69.50% | 2.00% | 5.20% |
| 72 | 46.70% | 1.60% | 3.90% |
| 144 | 29.50% | 0.50% | 1.40% |
| 264 | 0 | 0.30% | 0.50% |
| 336 | 0 | 0.80% | 0 |

TABLE 3

| Time (hr) | MCS1562 | BOCH | DOCH | BEOCH |
| --- | --- | --- | --- | --- |
| 0 | 100% | 100% | 100% | 100% |
| 24 | 87.2% | 87.5% | 89.3% | 88.4% |
| 48 | 77.6% | 79.2% | 79.6% | 79.9% |
| 80 | 64.7% | 64.9% | 67.8% | 68.0% |
| 144 | 38.4% | 36.1% | 40.6% | 46.4% |
| 194 | 13.1% | 20.0% | 22.7% | 25.7% |
| 246 | 0.0% | 0.1% | 0.2% | 6.9% |
| 336 | 0.0% | 0.0% | 0.0% | 0.0% |

TABLE 4

| Time (hr) | MCS1562 | DODOH |
| --- | --- | --- |
| 0 | 100% | 100% |
| 24 | 87.2% | 76.7% |
| 48 | 77.6% | 59.0% |
| 80 | 64.7% | 32.6% |
| 144 | 38.4% | 1.0% |
| 194 | 13.1% | 0.0% |
| 246 | 0.0% | 0.0% |
| 336 | 0.0% | |

TABLE 5

| Time (hr) | MCS1562 | KHOH | KPOH | MHOCH |
|---|---|---|---|---|
| 0 | 100% | 100% | 100% | 100% |
| 24 | 87.2% | 81.7% | 73.5% | 85.7% |
| 48 | 77.6% | 62.7% | 50.9% | 74.8% |
| 80 | 64.7% | 33.3% | 5.2% | 61.5% |
| 144 | 38.4% | 4.7% | 2.7% | 32.2% |
| 194 | 13.1% | 0.0% | 0.0% | 4.9% |
| 246 | 0.0% | 0.0% | 0.0% | 0.0% |
| 336 | 0.0% | | | |

TABLE 6

| Time (hr) | MCS1562 | BOBH |
|---|---|---|
| 0 | 100% | 100% |
| 24 | 85.8% | 84.1% |
| 48 | 73.3% | 72.0% |
| 90 | 48.6% | 45.0% |
| 142 | 21.5% | 17.3% |
| 187 | 0.0% | 4.0% |
| 235 | 0.0% | 1.7% |
| 264 | | 0.0% |

TABLE 7

| Time (hr) | MCS1562 | OMOO |
|---|---|---|
| 0 | 100% | 100% |
| 24 | 84.7% | 66.8% |
| 48 | 76.4% | 53.1% |
| 78.5 | 60.3% | 43.4% |
| 121 | 35.4% | 2.2% |
| 148 | 12.9% | 2.5% |
| 179 | 1.0% | 2.0% |
| 203 | 0.0% | 0.0% |

Although this invention has been described in terms of specific embodiments that are set forth in considerable detail herein, it should be understood that this description is by way of illustration only and that the invention is not necessarily limited thereto, since alternative embodiments and operating techniques will become apparent to those skilled in the art (in view of the disclosure). Accordingly, modifications are contemplated that can be made without departing from the spirit and scope of the described invention.

What is claimed is:

1. A functional fluid composition that generates reduced levels of carboxylic acid during use comprising:
   (a) a base stock comprising a phosphate ester, and
   (b) at least one acid scavenger selected from
      (i) epoxides of the formula

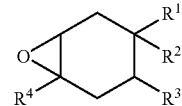

(ii) epoxides of the formula

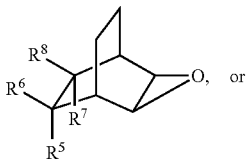

(iii) mixtures thereof;

wherein $R^1$, $R^2$ and $R^3$ are independently selected from H, and $-C(O)-R^{12}$, and wherein one or two of $R^1$, $R^2$ and $R^3$ are $-C(O)-R^{12}$; $R^4$ is selected from H or $-CH_3$; and $R^5$, $R^6$, $R^7$ and $R^8$ are independently selected from H, and $-C(O)-R^{12}$, and wherein one or two of $R^5$, $R^6$, $R^7$ and $R^8$ are $-C(O)-R^{12}$;

wherein; $R^{12}$ is an arylalkyl group having 7 to 12 carbon atoms.

2. The composition of claim 1 wherein said acid scavenger is an epoxide of formula (I).

3. The composition of claim 2 wherein one of $R^1$, $R^2$ and $R^3$ is $-C(O)-R^{12}$.

4. The composition of claim 2 wherein $R^1$ and $R^2$ are $-C(O)-R^{12}$.

5. The composition of claim 2 wherein $R^1$ and $R^3$ are $-C(O)-R^{12}$.

6. The composition of claim 2 wherein $R^4$ is H.

7. The composition of claim 1 wherein said acid scavenger is an epoxide of formula (II).

8. The composition of claim 7 wherein one of $R^5$, $R^6$, $R^7$ and $R^8$ is $-C(O)-R^{12}$.

9. The composition of claim 3 wherein said acid scavenger is

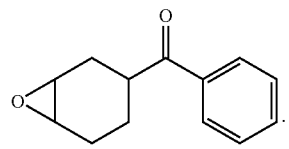

* * * * *

UNITED STATES PATENT AND TRADEMARK OFFICE
CERTIFICATE OF CORRECTION

PATENT NO. : 7,018,559 B2  
APPLICATION NO. : 09/851072  
DATED : March 28, 2006  
INVENTOR(S) : Jingen Zhang It is certified that error appears in the above-identified patent and that said Letters Patent is hereby corrected as shown below:

Col. 3, line 42, delete "—CH$_2$)$_n$," and replace with -- —(CH$_2$)$_n$ --

Col. 4, line 15, delete "exo-2,3-epoxynorbomane" and replace with

-- exo-2,3-epoxynorbornane --

Col. 7, line 40, delete "norbomene" and replace with -- norbornene --

Col. 10, line 59, delete "R$a$" and replace with -- R' --

Col. 14, line 38, delete "(3 x 150 niL)" and replace with -- (3 x 150 mL) --

Col. 15, line 7, delete "500 niL" and replace with -- 500 mL --

Col. 15, line 31, delete "100 niL" and replace with --100 mL --

Col. 18, line 1, delete "hexoxymnethyl" and replace with -- hexoxymethyl --

Col. 18, line 31, delete "500 nL" and replace with --500 mL --

Col. 19, line 44, delete "termperature" and replace with -- temperature --

Signed and Sealed this

Twelfth Day of December, 2006

JON W. DUDAS  
*Director of the United States Patent and Trademark Office*